(12) United States Patent
Lim et al.

(10) Patent No.: US 10,188,537 B2
(45) Date of Patent: Jan. 29, 2019

(54) APPARATUS FOR FOLDING OR UNFOLDING A MEDICAL IMPLANT, AND IMPLANT

(71) Applicant: VENUS MEDTECH (HANGZHOU), INC., Hangzhou (CN)

(72) Inventors: Hou-Sen Lim, Singapore (SG); Wolfgang Goetz, Regensburg (DE)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 364 days.

(21) Appl. No.: 14/891,261

(22) PCT Filed: May 14, 2014

(86) PCT No.: PCT/EP2014/059854
§ 371 (c)(1),
(2) Date: Nov. 13, 2015

(87) PCT Pub. No.: WO2014/184249
PCT Pub. Date: Nov. 20, 2014

(65) Prior Publication Data
US 2016/0250050 A1    Sep. 1, 2016

(30) Foreign Application Priority Data

May 14, 2013    (EP) .................................... 13002535

(51) Int. Cl.
*A61F 2/95*    (2013.01)
*A61F 2/24*    (2006.01)

(52) U.S. Cl.
CPC .............. *A61F 2/95* (2013.01); *A61F 2/2439* (2013.01); *A61F 2002/9511* (2013.01)

(58) Field of Classification Search
CPC .. A61F 2/2439; A61F 2/95; A61F 2002/9511; A61F 2/24; A61F 2/2418; A61F 2/2436; A61F 2/2427
See application file for complete search history.

(56) References Cited

U.S. PATENT DOCUMENTS

2005/0119722 A1    6/2005    Mikolaj et al.
2010/0286768 A1*   11/2010   Alkhatib ............... A61F 2/2418
                                                              623/2.11
(Continued)

FOREIGN PATENT DOCUMENTS

EP    2832318 A1    2/2015
EP    2918245 A1    9/2015
(Continued)

OTHER PUBLICATIONS

EP 13002535.6, Office Action, dated Oct. 7, 2015.
PCT/EP2014/059854, International Search Report, dated Aug. 18, 2014.

*Primary Examiner* — Eric J Rosen
*Assistant Examiner* — George J Ulsh
(74) *Attorney, Agent, or Firm* — Raymond Sun

(57) ABSTRACT

The present invention relates to an apparatus (100) for folding or unfolding at least one medical implant (300) by using at least one tension thread (11, 11'), wherein the apparatus (100) includes a shaft (1) including a reception area (55) for receiving the implant (300), and a tensioning device for altering a shape of the foldable and/or unfoldable implant (300) by the tension thread (11, 11').

10 Claims, 2 Drawing Sheets

(56) References Cited

U.S. PATENT DOCUMENTS

2011/0040366 A1    2/2011  Goetz et al.
2011/0040374 A1    2/2011  Goetz et al.

FOREIGN PATENT DOCUMENTS

| EP | 2918246 A1 | 9/2015 |
|----|------------|--------|
| WO | 2009/091509 A1 | 7/2009 |
| WO | 2011/101136 A1 | 2/2011 |
| WO | 2011/063972 A1 | 6/2011 |
| WO | 2012/084178 A2 | 6/2012 |

\* cited by examiner

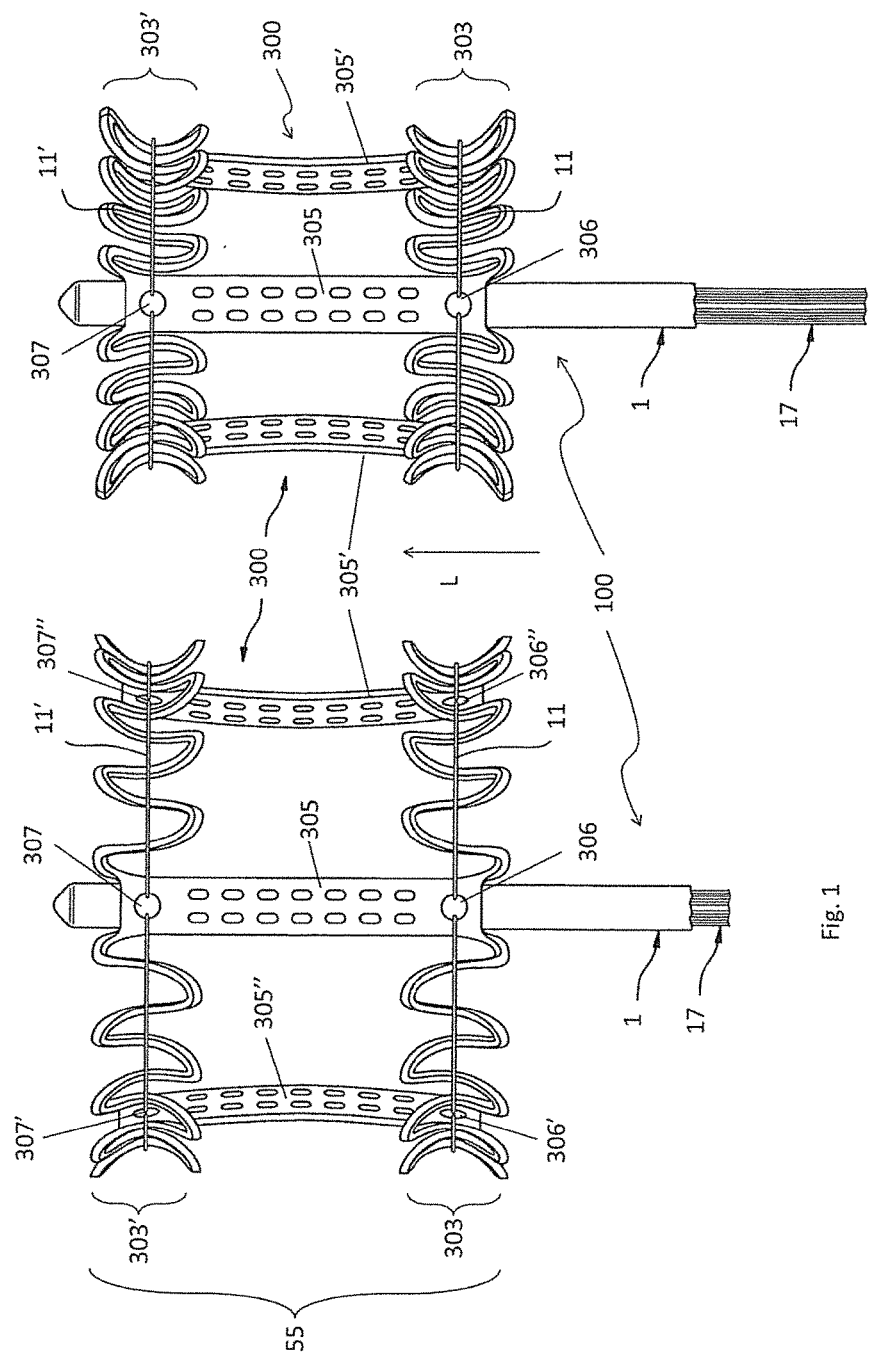

APPARATUS FOR FOLDING OR UNFOLDING A MEDICAL IMPLANT, AND IMPLANT

The present invention relates to medical implant (short hereinafter: implant) according to claim 1 for folding or unfolding an implant, and to an apparatus according to claim 6.

From practice, implants are known which may be folded or unfolded upon implantation by using one or several threads or filaments wound around the implant. Furthermore, corresponding apparatuses for folding and unfolding are known from practice.

One object of the present invention is to suggest an apparatus for folding or unfolding a foldable and/or unfoldable implant by using a tension thread. Furthermore, the present invention provides a suitable medical implant.

This object is solved by a medical implant having the features of claim 1.

According to the present invention the foldable and/or unfoldable medical implant comprises at least three tension threads for folding and/or unfolding the implant. It also comprises at least one first (mostly two) guiding structure for guiding some or all of the tension threads around the implant at an outside or an circumference thereof. Three, or preferably three, of the tension threads are wound along or around the outside or circumference of the implant (preferably at one longitudinal height or level of the implant) or one guiding structure in a manner such that each part of the outside or circumference is covered or contacted by exactly or not more than two tension treads and/or such that some or all of the tension threads each cover preferably about or exactly ⅔ ('two thirds') of the circumference of the implant. In certain embodiments according to the present invention, opening areas through which the tension threads are guided from an outside of the implant to an inside of the implant are not counted.

Also, the object of the present invention is solved by an apparatus for introducing and/or folding and/or unfolding an implant inside and/or outside the body of a patient by using at least one tension thread (referred to as singular or plural below). The apparatus according to the present invention includes a shaft having a reception area for receiving the implant.

The apparatus further includes at least one tensioning device for altering or amending a shape of the foldable and/or unfoldable implant by the tension threads or is connected to such a tensioning device.

In the following, the use of the expression "may be" or "may have", and so on, is to be understood synonymously with "in exemplary embodiments is" or "in exemplary embodiments has", respectively, and so on, and is intended to illustrate exemplary embodiments according to the present invention.

Exemplary embodiments according to the present invention are each also subject of dependent claims.

Exemplary embodiments according to the present invention may comprise one or more of the features named hereafter.

In some exemplary embodiments according to the present invention, altering the shape of the implant means reducing or increasing a diameter, particularly an external diameter, of the implant. Such an alteration may or may not involve an alteration of the implant's length or any other kind of alteration.

In certain exemplary embodiments according to the present invention, folding the implant means reducing the diameter of the implant. Folding also covers "re-folding" of an once expanded implant.

In some exemplary embodiments according to the present invention, unfolding should be understood as increasing the diameter of the implant, or as expanding.

In certain exemplary embodiments according to the present invention, the diameter of the implant is arranged in the reception area in a plane perpendicular to a main flow direction of the implant in case fluids flow through the implant after its implantation.

In some exemplary embodiments of the apparatus according to the present invention, the at least one tension thread is a thread. The thread may be a surgical suture thread or similar to it. The thread may have the shape of a rope, a filament or a cord. The thread may be designed as a chain having a plurality of engaging chain links.

In the following, the term thread or tension thread may also define a plurality of threads or tension threads whenever a person skilled in the art recognizes the exchangeability of the terms.

In certain exemplary embodiments according to the present invention, the shaft of the apparatus is rigid. In some exemplary embodiments according to the present invention, the shaft of the apparatus is flexible in one or more directions (i.e., in a longitudinal direction or in a direction of the width of the shaft, respectively, in both directions or in other directions). In certain exemplary embodiments, the shaft is elongatable. In particular exemplary embodiments according to the present invention, the shaft is stiff.

In certain exemplary embodiments according to the present invention, the implant is permeable for fluids in its implanted state in its longitudinal direction. "Permeable" means that the fluid may flow through the implant, for example, through an inner lumen thereof.

In some exemplary embodiments of the apparatus according to the present invention, the implant is—at least temporarily—mounted or loosely arranged on or at the reception area of the apparatus at the moment of unfolding or folding. In some of these embodiments, the implant is arranged on or at the reception area or is interconnected with the reception area only by the tension threads.

In certain exemplary embodiments of the apparatus according to the present invention, the tensioning device includes at least one pulling device. The pulling device is arranged and/or provided in such a way that it may indirectly or directly apply a tension on the implant for altering the shape of the implant by the tension thread if the pulling device is pulled by an operator (e. g., by the surgeon).

Alternatively or additionally, in some exemplary embodiments of the apparatus according to the present invention, the pulling device is arranged and/or provided in such a way that it may reduce a tension applied on the implant by the tension thread if the pulling device is pulled by an operator (e. g., by the surgeon).

In certain exemplary embodiments of the apparatus according to the present invention, the pulling device is arranged and/or provided such that it may interact with the tension thread in order to transfer force or tension.

In some exemplary embodiments of the apparatus according to the present invention, the pulling device and the tension thread are intricate with each other.

In certain exemplary embodiments according to the present invention, the term "intricate" is used to indicate that the tension thread is movable in at least one direction or in two directions relative to the pulling device.

According to some exemplary embodiments of the present invention, the term "movable" is to be understood as "slidable".

According to certain exemplary embodiments of the present invention, the term "intricate" means that the tension thread is movably arranged relative to the pulling device like a first link of a chain is movably arranged relative to an adjacent second link of this chain to which the first link is usually connected in a chain.

In some exemplary embodiments of the present invention, the term "intricate" shall indicate that the tension thread is simply crossed once with or wrapped around the pulling device or sections thereof.

In certain exemplary embodiments of the present invention, the transfer (or the transmittal, respectively) of force or tension between the pulling device and the tension thread is achieved by a non-form closure connection.

In some exemplary embodiments according to the present invention, the transfer of force or tension between the pulling device and the tension thread is achieved by a frictional connection.

In certain exemplary embodiments of the apparatus according to the present invention, the pulling device is embodied as at least one pulling thread or wire or consists of at least one pulling thread or wire.

In some exemplary embodiment of the apparatus according to the present invention, the tension thread and/or the pulling thread includes or constitutes at least one bundle or a plurality of threads or thread elements or consists thereof.

In certain exemplary embodiments according to the present invention, an interior of the shaft is permeable or may be passed in at least sections thereof in the longitudinal direction of the shaft. The shaft has a wall, and the shaft includes at least one shaft aperture through which tension threads for folding and/or unfolding the implant may enter and/or exit the inner lumen of the shaft.

In some exemplary embodiments according to the present invention, the implant is a stent or a cardiac valve assembly.

In particular exemplary embodiments according to the present invention, the apparatus comprises at least one implant according to the present invention, in particular, when connected with tension threads.

In certain exemplary embodiments according to the present invention, the shaft of the apparatus is permeable or has a passage for fluids in its interior in at least some sections of its longitudinal direction. The shaft has a wall defining an inner space, an interior or an inside or the shaft.

In some exemplary embodiments according to the present invention, the shaft includes at least one shaft aperture.

The at least one shaft aperture may preferably be arranged on a lateral area or on the circumference of the shaft rather than on the front side thereof.

In some exemplary embodiment of the present invention, the shaft of the apparatus includes a plurality of shaft apertures being uniformly or non-uniformly distributed along one or more circumferences and/or along the longitudinal extension of the shaft.

In certain exemplary embodiments according to the present invention tension threads for folding and/or unfolding the implant may enter and/or leave the apparatus through the shaft aperture.

In some exemplary embodiments according to the present invention, the apparatus is arranged for folding and/or unfolding an implant having the shape of a stent or a cardiac valve assembly.

In certain exemplary embodiments of the apparatus according to the present invention, the implant is a foldable and/or unfoldable implant.

In some exemplary embodiments according to the present invention, the apparatus is a catheter or a tip of a catheter that is provided to be interconnected with a catheter, preferably in a detachable manner.

In certain exemplary embodiments according to the present invention, the implant is—preferably by means of the tension threads or the tension threads alone—interconnected with a catheter tip attached or intended to be attached with the delivery device, e.g., the catheter, for implanting the implant. The catheter tip may be provided to be detachably attached or attachable to the catheter. The catheter according to the present invention may comprises the catheter tip or be attached to it, preferably in a detachable manner. This way, the implant can be stored in a wet surrounding until implantation whereas the catheter itself (i.e. the remaining parts thereof) does not necessarily have be stored in the wet container or condition as well.

In some exemplary embodiments according to the present invention, the apparatus may comprise a catheter tip as it is disclosed in WO 2011/101136 A1, the respective disclosure is expressly incorporated herein by reference thereto.

In particular exemplary embodiments according to the present invention, the apparatus is a catheter or any other implant delivery device comprising a handle assembly for folding or unfolding the implant by means of at least one tension thread, wherein the handle assembly comprises a force limiter. The force limiter may preferably comprise or consist of a drum for winding the tension thread thereon by rotating the drum; a knob to be rotated by a user of the handle assembly in order to fold or unfold the medical implant, the knob being interconnected with the drum such that the drum is rotated when the knob is rotated; and a force limiter for limiting the maximum force or tension that may be applied or is applicable to the tension thread or to the drum by rotating the knob.

In some exemplary embodiments according to the present invention, the apparatus may comprise a force limiter as it is disclosed in the patent application as filed in the name of the present applicant with the EPO (European Patent Office) having the filing number 13178719.4_on Jul. 31, 2013, the respective disclosure is expressly incorporated herein by reference thereto.

In certain exemplary embodiments according to the present invention, the implant is a heart valve comprising at least two leaflets; at least one crown piece interconnected to the leaflets, the crown piece preferably intended to be interconnected to a frame of a medical implant or a heart valve assembly; a top cuff; and a bottom cuff, the crown piece, the top cuff and the bottom cuff each being ring-shaped, and each of the top cuff and the bottom cuff being interconnected with the crown piece.

In some exemplary embodiments according to the present invention, the apparatus may comprise a heart valve as it is disclosed in the patent application as filed in the name of the present applicant with the EPO (European Patent Office) having the filing number 1416 0061.9_on Mar. 14, 2014, the respective disclosure is expressly incorporated herein by reference thereto.

In certain exemplary embodiments according to the present invention, the implant is a heart valve assembly comprising a frame and a heart valve, wherein the frame supports the heart valve or is interconnected thereto, preferably by sewing or sewing alone, the frame comprising at least a first guiding structure for guiding at least one tension thread for folding and/or unfolding the frame around or along the frame, preferably at an outside or an outer circumference of the guiding structure; at least a second guiding structure, different from the first guiding structure for guiding at least one tension thread for folding and/or unfolding the frame around or along the frame, preferably at an outside or an outer circumference of the guiding structure; at least two, preferably three, posts, the posts being arranged between the first and the second guiding structure in order to interconnect the first and the second guiding structure with each other and/or to maintain the distance between them; wherein the heart valve, comprises at least two leaflets; an interconnecting tissue interconnecting the leaflets with the frame; wherein the interconnecting tissue or parts thereof, respectively, is interconnected to at least one of the guiding structures such that it covers the guiding structure or parts thereof at an inner circumference of the guiding structure and such that it also covers at least both an upper part and a lower part of the outer circumference of the guiding structure.

In some exemplary embodiments according to the present invention, the apparatus may comprise a heart valve assembly as it is disclosed in the patent application as filed in the name of the present applicant with the EPO (European Patent Office) having the filing number 14160065.0_on Mar. 14, 2014, the respective disclosure is expressly incorporated herein by reference thereto.

In certain exemplary embodiments according to the present invention, tension is exerted on an implant by using at least one tension thread. The tension is preferably controlled by altering a length of the pulling device by which it extends out of the interior of the shaft or sections thereof.

In some exemplary embodiments according to the present invention, at least one of the apparatus and the comprises exclusively, i.e. only, (one or more) materials that are MRI (short for: magnetic resonance imaging) compatible. In certain exemplary embodiments according to the present invention, at least one of the apparatus and the implant comprises exclusively (one or more) materials that are not magnetic, ferromagnetic, or both. In some exemplary embodiments according to the present invention, at least one of the apparatus and the implant does not comprise metal or any metal alloy.

In certain embodiments according to the present invention, the medical implant further comprises at least a second guiding structure and at least (or exactly) three posts. The at least three posts are arranged between the first and the second guiding structures in order to connect them with each other and/or to maintain the distance between them. Each of the at least three posts has at least two openings through which tension threads are guided from an inside or inner space of the implant to an outside of the implant and back from the outside to the inside. The tension threads are guided to the outside through a first opening of a first one of the posts and back to the inside—or vice versa—through any second first opening of any second post, the first opening being different from the second opening, and the first post being different from the second post.

In some embodiments according to the present invention, one, many or every single tension threads cover or contact only—exactly or about—two thirds (corresponding to exactly or about 240°) of the periphery.

Please note that in certain embodiments according to the present invention some or all of the tension threads each cover about ⅔ of the circumference of the implant. In this calculation opening areas through which the tension threads are guided from an outside of the implant to the inside and which may reduce the periphery covered by two tension threads have not been counted. Hence, the periphery that has to be covered or that is covered by two tension threads is a bit less than 360°. Therefore, in some embodiments according to the present invention a two-thirds ('⅔') coverage may be understood such that the tension threads at issue extend only—preferably about or exactly—over two of three parts of the actually covered (by preferably two tension threads) section of the periphery.

In certain embodiments according to the present invention, the medical implant comprises exactly three posts.

In some embodiments according to the present invention, the medical implant further comprises a medical implant according to the present invention. In theses embodiments, the tensioning threads are guided around the first and/or the second guiding structure such that the circumference of the implant or the circumference of the its guiding structure(s) are covered or contacted by no more than, or by exactly, two tension threads during use.

In certain embodiments according to the present invention, the medical implant according to the present invention is a stent or a cardiac valve assembly.

In some embodiments according to the present invention, the apparatus according to the present invention comprises a medical implant according to the present invention.

In certain embodiments according to the present invention, an interior of the shaft is permeable or may be passed in at least sections thereof in the longitudinal direction of the shaft. The shaft has a wall. The shaft includes at least three shaft apertures—preferably iso-distant to the tip or end of the shaft, e.g. on the some longitudinal section or ring of the shaft—through which tension threads for folding and/or unfolding the implant may enter and/or exit. The tension threads are interconnected with the tensioning device of the apparatus. The tension threads are guided from an inside or inner space of the shaft to an outside of the shaft and back from the outside to the inside. The tension threads are guided to the outside through a first apertures and back to the inside—or vice versa—through a second aperture different from the first aperture.

In some embodiments according to the present invention, the apparatus comprises (preferably at least or exactly) three shaft apertures (preferably arranged at the same height or longitudinal level of the apparatus). Through each of the three apertures (preferably exactly) two tension threads enter or exit.

In particular embodiments according to the present invention, one, many or every single tension thread(s) re-enters the inner space of the implant through an aperture different from the one through which that tension thread has exited from the inner space to the outside of the implant, or vice versa.

In certain exemplary embodiments according to the present invention, all apertures are arranged on the same height or longitudinal level of the apparatus.

In certain exemplary embodiments according to the present invention, all instruments used for implanting or advancing the implant are MRI compatible.

Some or all advantages achievable by the apparatus according to the present invention may in certain exemplary embodiments of the present invention also be achieved by implant according to the present invention.

What is said in here with regard to one tension thread holds also true for a multitude of tension threads whenever this does stand in contrast to the general idea of the present invention.

Some or all exemplary embodiments according to the present invention may provide for one, several or all of the advantages named above and/or hereafter.

According to the present invention an optimum between friction and redundancy regarding provision of tension threads. With former designs of foldable and unfoldable implants by the inventors of the present invention tried to provide for a redundancy of tension threads wound around the periphery of the implant as a safety measurement. Redundancy means that each part of the periphery could be re-folded or unfolded if needed even in the—albeit very unlikely event—that one of the tension threads break since each part of the periphery was covered by three tension threads. However, the friction due to the contact of the tension thread and the implant along the periphery thereof that has to be overcome upon withdrawing the tension threads once they have been cut or otherwise separated from the implant has turned out to be too high to allow for certain constructional designs.

Reducing the number of threads from three to just two tension threads covering the single sections of the periphery has led to a by far lower friction. The lower friction allows new technical solutions regarding the pulling device, the dimensions of the pulling device, the overall size of the apparatus and the like. At the same time, there is still redundancy in the sense described supra.

Also, with a ⅔-coverage as described herein, one can afford to have one string or tension thread to break and will still be able to crimp the stent entirely. Also, friction is within a reasonable range.

Providing at least one of the apparatus and the implant to be MRI compatible allows advantageously for controlling the location and orientation of the apparatus or the implant, or both, by MRI upon use of the apparatus or implantation of the implant. No heat, sparks or artefacts are generated during MRI because of the materials chosen for the apparatus or the implant.

In the following, examples of the present invention will be described with reference to the accompanying figures wherein similar or identical assemblies or elements are denoted by same reference numbers.

FIG. 1 shows schematically simplified and in part section an apparatus according to the present invention with an expanded implant according to a first exemplary embodiment of the present invention;

FIG. 2 shows the apparatus of FIG. 1 with the implant in a further (partly) folded condition;

Figure 3:
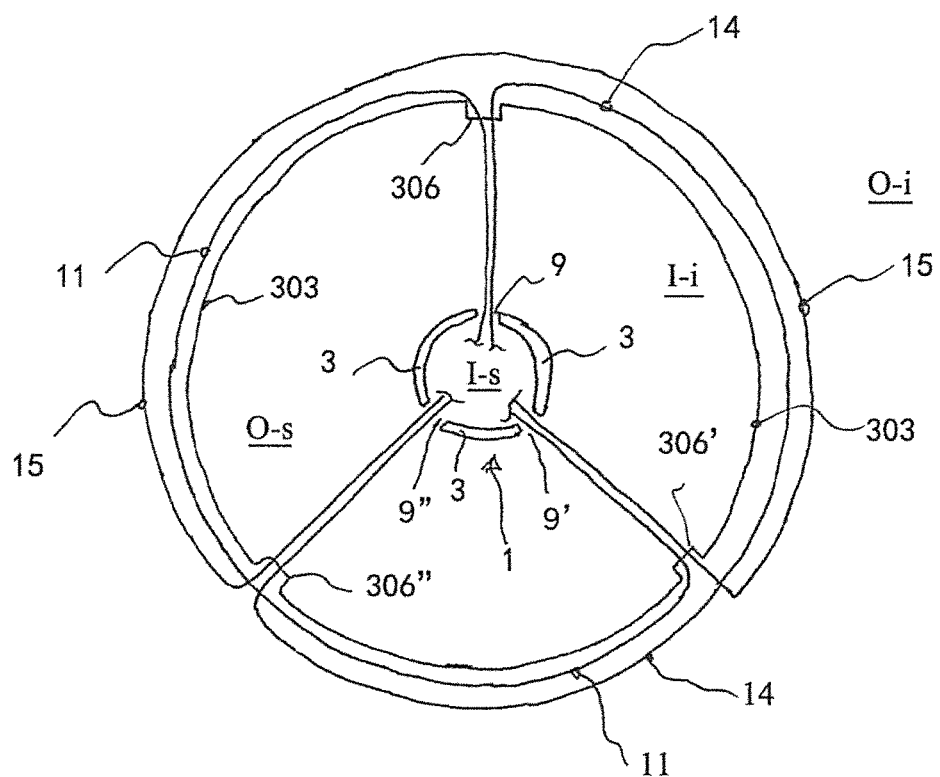
FIG. 3 shows a cut through the tip of an apparatus of FIG. 1 of an apparatus in top view, the tip being cut at the level of its first guiding structure.

FIG. 1 shows schematically simplified and in part section an apparatus 100 according to the present invention with an expanded implant 300 according to a first exemplary embodiment of the present invention. The implant 300 is arranged at a reception or retaining area 55 of the apparatus 100 for receiving the implant 300.

A first tension thread 11 and a second tension thread 11' are arranged around the implant 300. As can be seen from FIG. 1, the implant 300 comprises a first guiding structure 303 for guiding the first tension thread 11 and a second guiding structure 303' for guiding the second tension thread 11'.

In the exemplary embodiment of FIG. 1, the first guiding structure 303 and the second guiding structure 303' are designed as rings or channel-like ring structures. These structures are optionally radially open but medially closed as it is exemplarily also shown in FIG. 1.

In the exemplary embodiment of FIG. 1, the first guiding structure 303 and the second guiding structure 303' are connected to each other by three posts 305, 305' and 305".

In the example of FIG. 1, the threads 11 and 11' are provided for holding the implant 300 with regard to the apparatus 100. In any case, the diameter of the implant 300 or of its folding state may be altered by varying the tension of the threads 11 and 11' as will be explained in more detail below.

The apparatus 100 has a shaft 1 having a lumen covered by a wall (depicted with reference numeral "3" in FIG. 3). In the lower area of FIG. 1, the wall of shaft 1 is longitudinally cut. Pulling threads 17 arranged within the lumen of the shaft 1 extend therefrom.

The pulling threads 17 are integral with or interconnected to threads 11 and 11' which are guided along the circumference of implant 300 at different longitudinal levels (along the longitudinal direction L of the implant 300, wherein the arrow L also indicated the longitudinal direction of the apparatus 100 and/or its shaft 1)—by the first and the second guiding structure 303 and 303'—thereof such that pulling or releasing the pulling threads 17 makes the threads 11 and 11' to exert more or less force on the implant 300 as it is also described in the patent application published under WO 2011/063972 A1. This way, operating the pulling threads 17 may provide for a change in one or more cross-section dimensions of the implant 300. The respective disclosure of WO 2011/063972 A1 is incorporated into the present specification by reference.

The threads 11 and 11' enter into the lumen of shaft 1 by apertures not shown in FIG. 1 (but part of which are shown in FIG. 3 as apertures 9, 9' and 9") and they exit shaft 1 from such apertures again.

The expansion of implant 300 may benefit in the present exemplary embodiment from the internal stress or from shape-memory capacities of implant 300. The implant 300 may be manufactured from Nitinol or comprise such material. In order to expand the implant 300, the pulling threads 17 need, however, to be sufficiently released. For folding the implant 300 again, the pulling threads 17 are tightened again.

Supra, the number of tension threads has been set to three. However, as can been from FIG. 1, the implant may also have any multitude of three (e. g., six, or nine) tension threads. In practice, the implant according to the present invention will have three tension threads at one or each longitudinal level of the implant or the shaft.

FIG. 2 shows the apparatus 100 of FIG. 1. The implant 300 is in a partly folded condition (also referred to herein as "folded" or "refolded"). Since folding of the implant 300 has to be achieved by pulling the pulling threads 17, in FIG. 2 the pulling threads 17 protrude further out of shaft 1 than in FIG. 1.

In FIG. 1 (and likewise in FIG. 2), apparatus 100 is shown with only one upper ("second") thread 11' and one lower ("first") thread 11. This reduction (simplification) is used for improved clarity. It is therefore obvious that any arbitrary number of upper and lower threads 11 and 11' may be provided ("upper" and "lower" relate to the upright position of the implant shown in FIG. 2). A corresponding number of apertures 9, 9' and 9" may be provided. In preferred embodiments, three tension threads 11, 14 and 15 are provided around the first guiding structure 303, and three tension threads 11', 14' and 15' are provided around the first guiding structure 303'.

FIG. 3 shows a cut through the tip of an apparatus of FIG. 1 of an apparatus in top view, the tip being cut at the level of its first guiding structure 303'.

The implant 300 is represented by the shaft 1 comprising three apertures 9, 9' and 9", a schematically shown first guiding structure 303 and openings 306', 306' and 306" of the otherwise not shown posts 305, 305' and 305" (the posts are, however, shown in FIG. 1).

At an outside of the first guiding structure 303, three (first) tension threads 11, 14 and 15 are wound around the circumference of the implant 300 such that the circumference is covered or contacted by exactly two tension threads, either 11 and 15 (see left hand side), 11 and 14 (see below in FIG. 3) or 14 and 15 (see right hand side). This way, each part of the circumference is always covered by two tension threads.

In the exemplary embodiment of FIG. 3, each of the tension threads 11, 14 and 15 covers about ⅔ (or about 240°) of the entire circumference of the implant 303 (or its guiding structure 303'). Each of the tension threads 11, 14 and 15 extends from an inside of the shaft 1 through a first aperture, for example aperture 9, to a first opening, for example, opening 306 of a first post 305 around about ⅔ of the periphery and through a second opening, for example opening 306', of a second post, for example post 305' back into the inner space of the implant 300 and through a second aperture, for example, aperture 9' back into the inner space of the shaft 1. For the sake of clarity, inside the inner space of shaft 1, all tension threads are indicated as cut.

Please note that the tension threads cover about ⅔ of the circumference in the embodiment of FIG. 3. In this calculation opening areas through which the tension threads are guided from an outside of the implant to the inside and which may reduce the periphery covered by two tension threads have not been counted. Hence, the periphery that is covered by two tension threads is a bit less than 360°. Therefore, in some embodiments according to the present invention a two thirds coverage may be understood such that the tension threads at issue extend only over two of three parts of the actually (by two tension threads) covered section of the periphery.

The example of FIG. 3 relates to the tension threads 11, 14 and 15 wound around the first guiding structure 303. However, what has been described or shown therewith may in certain embodiments also be true for tension threads 11', 14' and 15' wound around the second guiding structure 303' (see FIG. 1 or FIG. 2).

In the illustration of FIG. 3, the tension threads 11, 14 and 15 are all shown to have a certain distance to the first guiding structure 303 for the sake of clarity only. Obviously, during use, all these tension threads contact the first guiding structure 303 and apply tension onto the latter acting against the implants attitude to unfold following its shape-memory abilities.

The reference sign I-i relates to the inner space or inside of the implant 300, I-s to the inner space or inside of the shaft 1, O-i to the outside of the implant 300, and O-s to the outside of the shaft 1.

REFERENCE NUMERALS 100 apparatus
1 shaft
3 wall of shaft 1
9 aperture
9' aperture
9" aperture
11 first tension thread(s), also 14, 15
11' second tension thread(s), also 14', 15'
17 pulling thread
55 reception or retaining area
300 implant
303 first guiding structure of the implant
303' second guiding structure of the implant
305 post
305' post
305" post
306 opening
306' opening
306" opening
307 opening
307' opening
307" opening
I-i inner space or inside of the implant
I-s inner space or inside of the shaft
L longitudinal direction
O-i outside of the implant
O-s outside of the shaft

The invention claimed Is:

1. A foldable and/or unfoldable medical implant comprising:
at least three tension threads for folding and/or unfolding the implant; and
at least one first ring having a channel for guiding some or all of the tension threads around the implant at an outside or an circumference thereof, wherein three of the tension threads are wound along or around the outside or circumference of the implant in a manner such that each part of the outside or circumference is covered or contacted by two of the tension treads,
the medical implant further comprises at least a second ring having a channel, and at least three posts, the at least three posts being arranged between the first ring and the second ring in order to connect them with each other and/or to maintain the distance between them, each of the at least three posts having at least two openings through which the tension threads are guided from an inside of the implant to an outside of the implant and back from the outside to the inside, wherein the tension threads are guided to the outside through a first opening of a first one of the posts and back to the inside through a second opening of a second one of the posts, the first opening being different from the second opening, and the first post being different from the second post.

2. A medical implant according to claim 1, comprising exactly three posts.

3. A medical implant according to claim 1, wherein the tensioning threads are guided around the first ring and/or the second ring such that each part of the first ring and/or the second ring is covered or contacted by two of the tension threads.

4. A medical implant according to claim 1, wherein the implant is a stent or a cardiac valve assembly.

5. An apparatus comprising the at least one medical implant of claim 1, and is configured to fold or unfold the at least one medical implant by altering the tension applied to the medical implant by means of six tension threads, wherein the apparatus includes or is connect to: a shaft including a reception or retaining area for receiving the implant; and a tensioning device for altering a shape of the foldable and/or unfoldable implant that is connected and arranged to apply tension onto the medical implant via all six tension threads.

6. An apparatus according to claim 5, wherein an interior of the shaft is permeable or may be passed in at least sections thereof in the longitudinal direction of the shaft, wherein the shaft has a wall, wherein the shaft includes at least three shaft apertures through which tension threads, for folding and/or unfolding the implant may enter and/or exit, wherein tension threads for folding and/or unfolding of the implant are interconnected with the tensioning device of the apparatus,
    wherein the tension threads are guided from an inside of the shaft to an outside of the shaft and back from the outside to the inside, wherein the tension threads are guided to the outside through a first aperture of the shaft apertures and back to the inside through a second aperture of the shaft aperture, wherein the first and the second apertures are different from each other.

7. An apparatus according to claim 5, wherein the apparatus comprises three shaft apertures, and wherein through each of the three apertures two tension threads enter or exit.

8. An apparatus according to claim 5, wherein an interior of the shaft is permeable or may be passed in at least sections thereof in the longitudinal direction of the shaft, wherein the shaft has a wall, wherein the shaft includes at least three shaft apertures through which tension threads for folding and/or unfolding the implant may enter and/or exit, wherein tension threads for folding and/or unfolding of the implant are interconnected with the tensioning device of the apparatus, wherein the tension threads are guided from an inside of the shaft to an outside of the shaft and back from the outside to the inside, wherein the tension threads are guided to the outside through a first apertures and back to the inside through a second aperture, wherein the first and the second apertures are different from each other.

9. An apparatus according to claim 5, wherein the apparatus comprises three shaft apertures, and wherein through each of the three apertures two tension threads enter or exit.

10. A medical implant according to claim 1, comprising exactly three posts.

\* \* \* \* \*